United States Patent
Dettmann et al.

(10) Patent No.: US 7,262,850 B2
(45) Date of Patent: Aug. 28, 2007

(54) METHOD FOR INSPECTION OF PERIODIC GRATING STRUCTURES ON LITHOGRAPHY MASKS

(75) Inventors: Wolfgang Dettmann, Munich (DE); Roderick Koehle, Ottobrunn (DE); Martin Verbeek, Munich (DE)

(73) Assignee: Infineon Technologies AG, Munich (DE)

( * ) Notice: Subject to any disclaimer, the term of this patent is extended or adjusted under 35 U.S.C. 154(b) by 346 days.

(21) Appl. No.: 10/735,414

(22) Filed: Dec. 12, 2003

(65) Prior Publication Data

US 2004/0165763 A1   Aug. 26, 2004

(30) Foreign Application Priority Data

Dec. 12, 2002   (DE) ............................. 102 58 371

(51) Int. Cl.
    *G01B 11/00*   (2006.01)
(52) U.S. Cl. .................................... 356/399
(58) Field of Classification Search ... 356/237.2–237.5
    See application file for complete search history.

(56) References Cited

U.S. PATENT DOCUMENTS

| | | | | |
|---|---|---|---|---|
| 3,658,420 A * | 4/1972 | Axelrod | ........................ | 356/71 |
| 3,972,616 A * | 8/1976 | Minami et al. | ................ | 356/71 |
| 4,595,289 A * | 6/1986 | Feldman et al. | .......... | 356/237.5 |
| 5,838,433 A * | 11/1998 | Hagiwara | .................... | 356/364 |
| 5,905,572 A * | 5/1999 | Li | ................. | 356/479 |
| 6,268,093 B1 * | 7/2001 | Kenan et al. | .................. | 430/30 |
| 6,630,996 B2 * | 10/2003 | Rao et al. | ................. | 356/237.5 |
| 6,879,391 B1 * | 4/2005 | Danko | ........................ | 356/237.4 |
| 2004/0086167 A1 * | 5/2004 | Jun et al. | ..................... | 382/141 |

* cited by examiner

*Primary Examiner*—Tarifur R. Chowdury
*Assistant Examiner*—Isiaka O. Akanbi
(74) *Attorney, Agent, or Firm*—Slater & Matsil, L.L.P.

(57) ABSTRACT

The invention relates to a method for inspection of periodic structures on lithography masks using a microscope with adjustable illumination and an operating element for movement of a mechanical stage with the lithography mask attached to it in order to record images of the lithography mask at a computer-controlled location on the lithography mask. The position, the size and the pitch specification of the lithography mask are stored.

21 Claims, 6 Drawing Sheets

METHOD FOR INSPECTION OF PERIODIC GRATING STRUCTURES ON LITHOGRAPHY MASKS

TECHNICAL FIELD

The present invention relates generally to masks and, more preferably, to a method for inspection of periodic grating structures on lithography masks.

BACKGROUND

As is known in microlithography, semiconductor structures are produced by the imaging of a structure which has previously been produced on a lithography mask on a wafer that is coated with a photoresist and by exposure and subsequent development of the photoresist.

After the manufacture of the lithography mask, the mask has different properties, which vary from mask to mask. These different properties have a considerable influence on photolithography and on the imaging thereof. In this case, a distinction is drawn between general (global) and local properties which are normally specified.

Global properties are, for example, the error in the line width (CD target value) from the target size (offset error), as well as the fluctuation in the error over the image area (uniformity error). In alternating phase masks, there are structures which have phase-shifting properties when illuminated with coherent light. These phase shifts are produced by etching the relevant structures into the glass. Undesirable brightness errors occur due to discrepancies from the ideal etching depth, and these likewise represent a global mask property.

Local properties are defects on the mask which occur either due to faults in the production of the mask or due to subsequent impurities, e.g., dust.

The aim when producing lithography masks is to produce a lithography mask that satisfies a number of requirements. With respect to the local properties, currently the masks are tested by process inspection and quality measurements.

At present, systematic manufacturing faults in lithography masks such as regular errors in the line separation (offset target error) and changes in the line width (uniformity error) are measured directly on the structures by means of different SEM measurements (Scanning Electron Microscopy) at a large number of points on the mask. However, this is a time-consuming and unreliable assessment process, since the measurement errors and the poor reproducibility of SEM measurements are disadvantageous. For example, the direction of an electron beam significantly influences the measurement result. For this reason, this method is not suitable for lithography masks which are etched in quartz, since there are no well-defined etchings for SEM measurement in masks such as these.

Mask assessment for new mask technologies, such as interference masks, is very difficult. Interference masks contain trenches which have been etched in the mask and which produce diffraction (phase shifting) of the light that is passed through. However, no known method exists for determination of the diffraction and transmission parameters.

A combination of a depth measurement and of an optical measurement using an MSM microscope (Microlithography Simulation Microscope) is used. The measurement values which are obtained with a microscope such as this are compared with line width measurements of structured wafers in order to obtain information about the value of the newly produced lithography masks.

A further aim is to make improvements in defects inspection. Since some defects on the lithography mask are transferred to the chips formed on the wafer, it is very important to ensure an error-free mask structure. Since each process step during mask manufacture unavoidably generates some defects in the lithography mask, it is necessary to be able to inspect and to repair lithography masks.

During mask inspection, the lithography mask is examined for defects, and the defects which are found are classified on the basis of their importance for the lithography and their influence on the functionality of the chip. Mask defects which endanger the functionality and the reliability of the chip function must necessarily be repaired.

The test devices which are currently used employ laser scanning microscopy in order to check lithography masks for defects. In this case, the mask surface is scanned with a laser beam, and the reflected and transmitted light is measured. In defect-free areas, the sum of the reflected light and of the transmitted light is greater than a predefined value. In contrast, in the event of defects, the light is scattered, so that the sum of the intensities is less than the predefined value.

In the case of high-end masks, this approximation is extended in various ways, for example by using an adjacent chip as a reference for the "die-to-die" inspection rather than comparison with a constant reference signal ("die-to-database").

For standard quality masks, this approximation is simple and efficient in terms of the inspection time and the costs. For high-end masks and in particular for interference masks, this approximation suffers from the fact that masks such as these use a different, shorter wavelength for the first lithography step than that used for the final lithography step. However, since a shorter wavelength means poorer resolution, the sensitivity with respect to defects is also less than during the final lithography process.

Another problem with the laser scanning method is that the interference masks (diffraction gratings) are seen very differently during laser scanning and during optical imaging.

One solution to this problem is to simulate the lithographic process by means of a modified microscope. Lithography microscopes of this type are referred to by the product name MSM (Microlithography Simulation Microscope) and are offered, for example, by the company ZEISS. MSM has the advantage of using the same wavelength as that used for the lithography process, the same illumination of the lithography mask, and the same optical presets for the aperture angle of the projection optics.

In contrast to lithographic exposure, in which the image of the lithography mask is reduced in size, MSM magnifies the image of the lithography mask onto a sensor. However, MSM can image only a small section of the mask at one time.

If the lithography mask is scanned step-by-step, it is possible to record images of it which essentially correspond to the intensity with which a wafer would be exposed.

If a fault has a severe influence on the exposure of the resist, this would be evident from the air image which has been recorded by the MSM. However, in order to make it possible to use the microscope for inspection, an error signal is required which signals the defect. The lithography mask must therefore have various identical chip layouts so that the microscope can compare these images in pairs.

The disadvantage of this method is that each image is influenced by general noise, and that the final error image is subject to greater noise.

Another disadvantage of this method is its complexity, since the entire image of a die must be scanned into the memory of the computer, must be adjusted, and must be compared. This necessitates considerable memory volume as well as considerable computation time.

Upon insertion into a mask stage, an image is generally rotated slightly with respect to the sensor. This mask method can determine and correct the rotation of the mask and the magnification factor of the mask with high accuracy. If the magnification and image rotation are known, the Fourier coefficients can be determined. A reconstructed, noise-free image is obtained by back-transformation by means of a Fourier series.

SUMMARY OF THE INVENTION

The preferred embodiment of the invention provides a method for characterizing the global properties of a mask and identifying local image errors. In one aspect, the present invention relates to a method for inspection of periodic structures on lithography masks using a microscope with adjustable illumination and an operating element for movement of a mechanical stage with the lithography mask attached to it. In order to record images of the lithography mask fat a computer-controlled location on the lithography mask, the position, the size and the pitch specification of the lithography mask are stored.

One major advantage of performing Fourier analysis on the image, compared with die-to-die inspection, is that less computation complexity (memory and computer capacity) is required, thus resulting in cost and time savings. In addition, better sensitivity is achieved since only one noisy image need be compared.

It is also possible to measure equalization errors in interference masks. In this case, it should be remembered that it is impossible to characterize masks by means of the conventional die-to-die inspection algorithms.

It is also possible to determine the mask's critical dimension (CD) from the intensity of the higher Fourier coefficients.

The only disadvantage of this method is that a restriction to periodic structures is necessary. It should be remembered, however, that the restriction to periodic structures is easily compensated for by better sensitivity and less stringent requirements for faster and cheaper computers.

The two methods can also be combined with one another, so that the dense structures are inspected by means of Fourier analysis and the peripheral, less dense structures are inspected by die-to-die inspection.

In addition to fault inspection, the algorithm is also suitable for characterization of the mask. The range of the "off-target" error of the Cr line width of the mask can be determined.

For this purpose, the amplitude of the Fourier coefficients of the main feature location is compared with a reference value. If the value is smaller/less than the reference value, then the mask has a large positive/negative mapping error. It is also possible to determine the mask's CD uniformity. Very accurate characterization of the entire surface of the mask is achieved by repetition of this measurement at a large number of locations.

In the case of masks based on interference technology, the diffraction parameters (phase shift parameters) and the transmission errors can be determined by means of this analysis method.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF ILLUSTRATIVE EMBODIMENTS

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

Various embodiments of the present invention will now be described. After a written description, specific examples will be described with respect to the Figures.

In a first aspect, the present invention provides for the calibration of a first image of each array structure for selected locations on the lithography mask, calculation of the Fourier coefficients at a reference point of an array/diffraction grating, calculation of a residual image from a difference between an original image of the array structure and Fourier expansion, and formation of a threshold value for the calculation of an image indicating an error.

The Fourier coefficients are a complete description of the optical properties of a periodic structure which is of high quality and accuracy owing to averaging over the image area. In order to characterize the specific imaging properties of alternating phase masks (interference masks), the image intensity must be recorded by defocusing.

The calibration can be carried out by determination of the mask rotation and determination of the magnification. The aim of the calibration is to determine the angle of the mask rotation with as high a numerical accuracy as possible.

The rotation angle and the magnification are preferably determined by numerical optimization, that is by choosing the rotation angle and the magnification factor such that the magnitude of the associated Fourier coefficient is a maximum.

A frequency filter is preferably used in order to reduce curling in the calculation of the residual image.

In a further development of the invention, the Fourier coefficients are determined and calculated using an error determination algorithm, with the Fourier coefficients of the main position being measured at a large number of locations on the mask. The Fourier coefficients are then converted to a line width value by means of back-transformation and a predetermined intensity threshold value, so that a mean value of the error in the line width is determined by formation of an average value over all the measurement points. The lithography mask is rejected if the error in the line width is greater than a predetermined threshold value.

A further refinement of the invention provides that, in order to determine the phase error, each mask position is recorded using different focal lengths. Subsequently, the width of the image lines and their separations are measured by use of Fourier analysis. The error from the defocusing is determined from the difference between the adjacent intermediate spaces when the error exceeds a predetermined threshold value.

An error image can be calculated from the noise-free image and from the original measurement by formation of differences. Since the main feature is now absent, coarse image errors can be easily identified by means of the threshold value detector. Only one in-focus recording is necessary for defect inspection.

A method for producing lithography masks is also characterized by coating, developing, etching, inspecting, and repairing the lithography mask. The lithography mask may be a chromium mask, a half-tone maks, or an interference mask.

Inspecting involves calibrating a first image of each array structure for selected locations on the lithography mask, calculating Fourier coefficients at a reference point of an array/diffraction grating, calculating a residual image from a difference between an original image of the array structure and a Fourier expansion, and forming a threshold value for the calculation of an image indicating an error; and repairing the lithography mask based upon results of the inspecting.

The repairing can be carried out by means of ion etching or by use of an atom microscope for microprocessing of the lithography mask.

One concept of this invention is to make use of the fact that, in the case of memory chips, the majority of the design is composed of regular structures that are similar to an array. These array structures are at the same time the structures with the most stringent requirements for quality of the line widths, for defect inspections, and for repairs based thereon.

If the position (e.g., vertical and horizontal) of an array is predetermined, this array can be inspected by means of a Fourier analysis of the microscope image. The remaining area of the mask can then be inspected either by means of one of the already mentioned die-to-die inspection methods or by means of conventional laser inspection with poorer resolution.

Figure 1A:
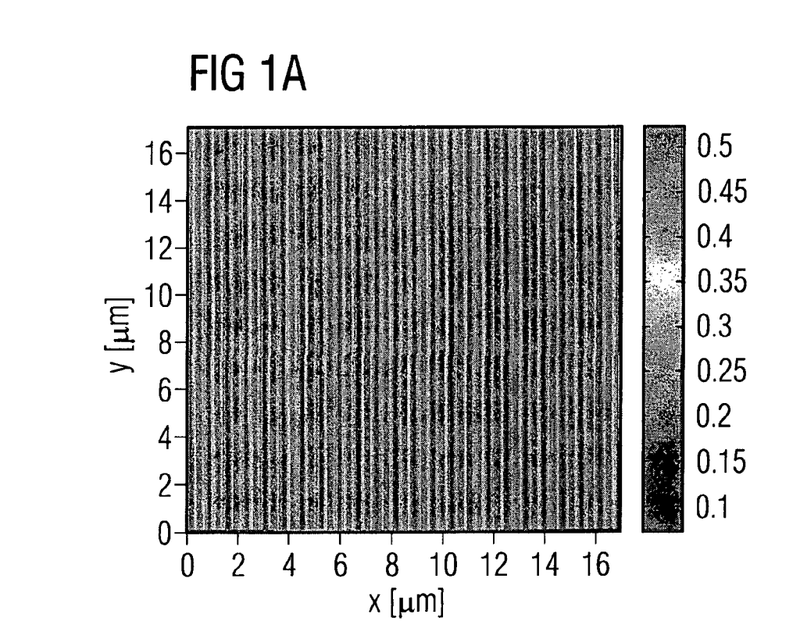
FIG. 1A shows an image of a dense line pattern of a mask.

FIG. 1A shows line patterns for an interference mask with a separation (pitch) of 720 nm recorded using an MSM-193 microscope. For an infinite periodic grating network, the Fourier transformation results in a discrete grating with a frequency, for example, of 1/pitch. Since the grating in the example is not infinite, the resultant spectral lines are limited by the resonant frequency of the image boundary.

Figure 1B:
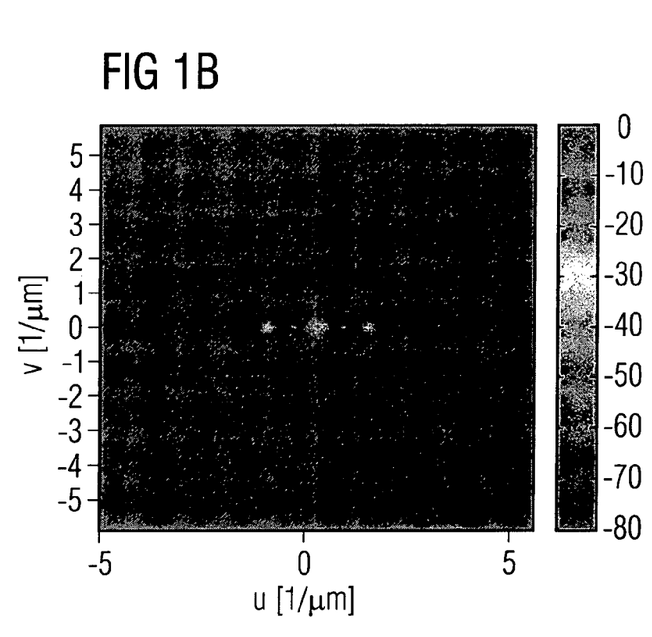
FIG. 1B shows the reproduction of the mask shown in FIG. 1A after Fourier transformation has been carried out.

In this example, the pitch of the grating is 720 nm, and it can be seen from the Fourier image that the grating results in a steep spike at a frequency of $1/720$ nm. A weak spike at a frequency of $1/1440$ nm can be seen in the Fourier image of FIG. 1B. This is a specific property of interference masks which may have such an (undesirable) intensity disturbance.

In an example of a calculation of the spike amplitude of the main feature, a reference pattern can be calculated by inverse Fourier series expansion.

Figure 2:
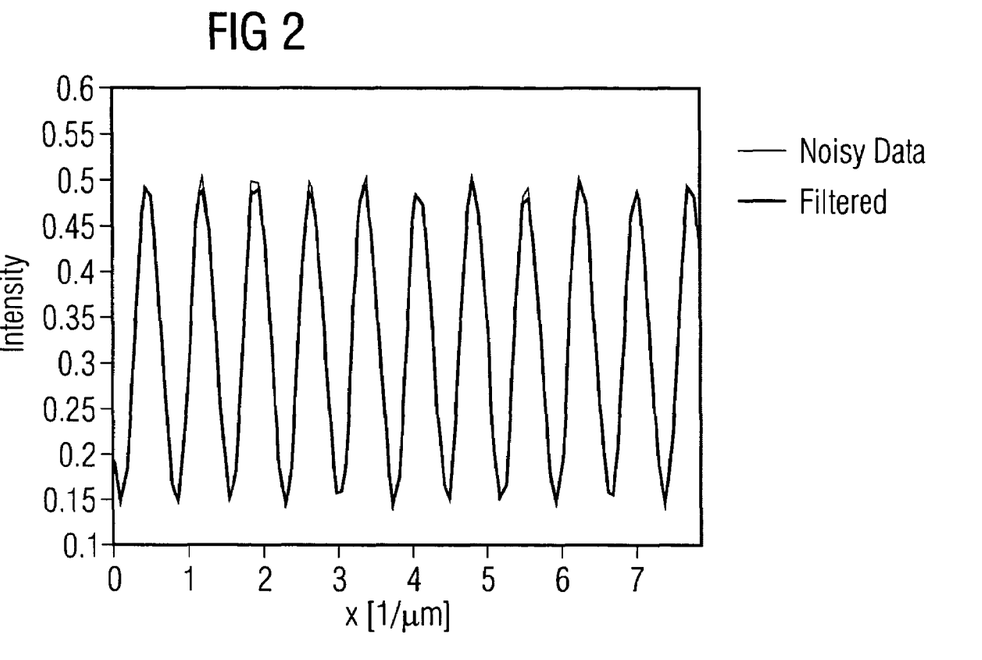
FIG. 2 shows intensity functions of an original image measured with and without filtering of the data.

FIG. 2 shows the result of the reconstructed signal which is obtained with Fourier coefficients for a fundamental frequency of $1/720$ nm and $1/1440$ nm. The difference between the measured image and the Fourier reconstruction results in an error image which can be used for fault detection.

Figure 3A:
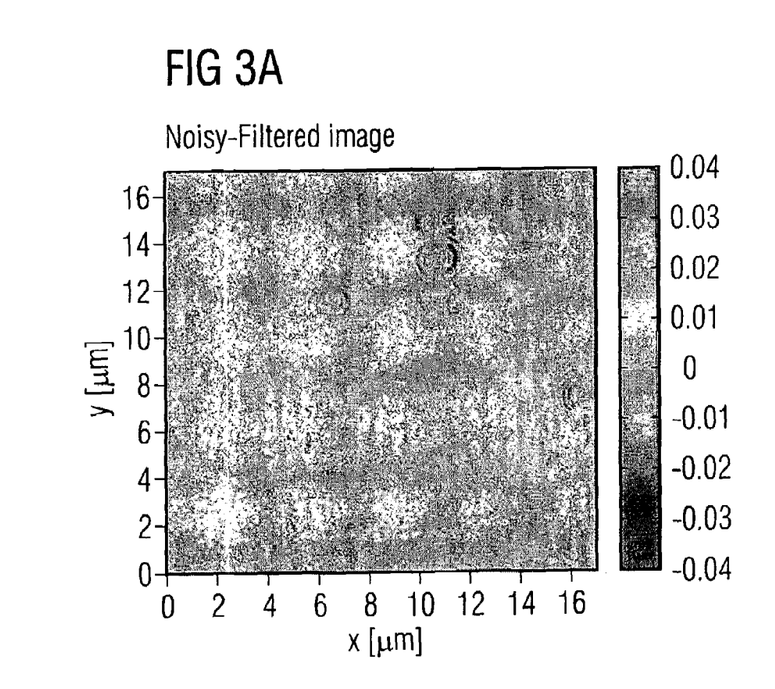
FIG. 3A shows a fault image before image processing.
Figure 3B:
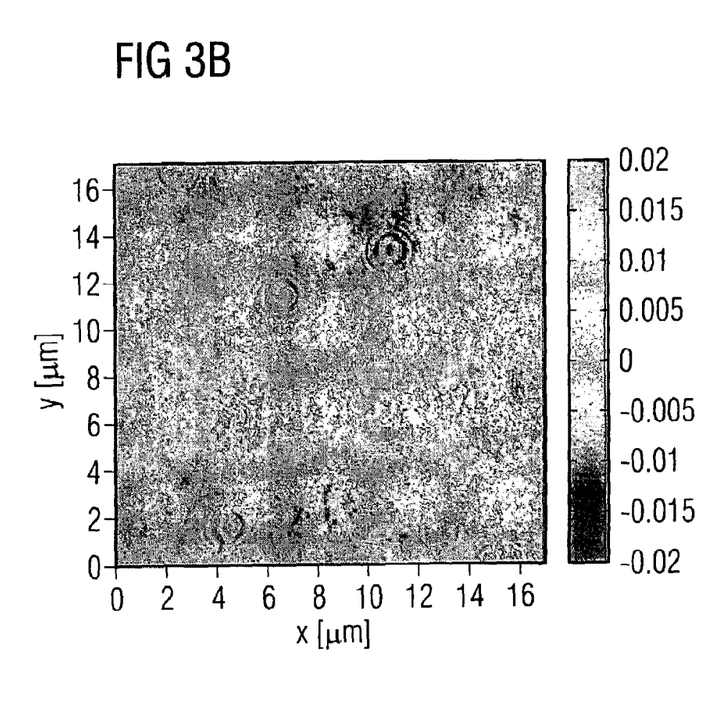
FIG. 3B shows the fault image from FIG. 3A after image processing with clearly visible patterns in the form of waves, which are caused by imaging errors in the camera.

FIG. 3B shows the resultant error image after the subtraction of the Fourier reference from the measured image of FIG. 3A. As can be seen, there is slight curling in the grating period, or a number of patterns in the form of waves, which result from imaging errors in the camera. The curling can be reduced further and the contrast of the defect can be increased further by use of a second filter step, which uses an annular bandpass filter around the grating frequency.

Figure 6A:
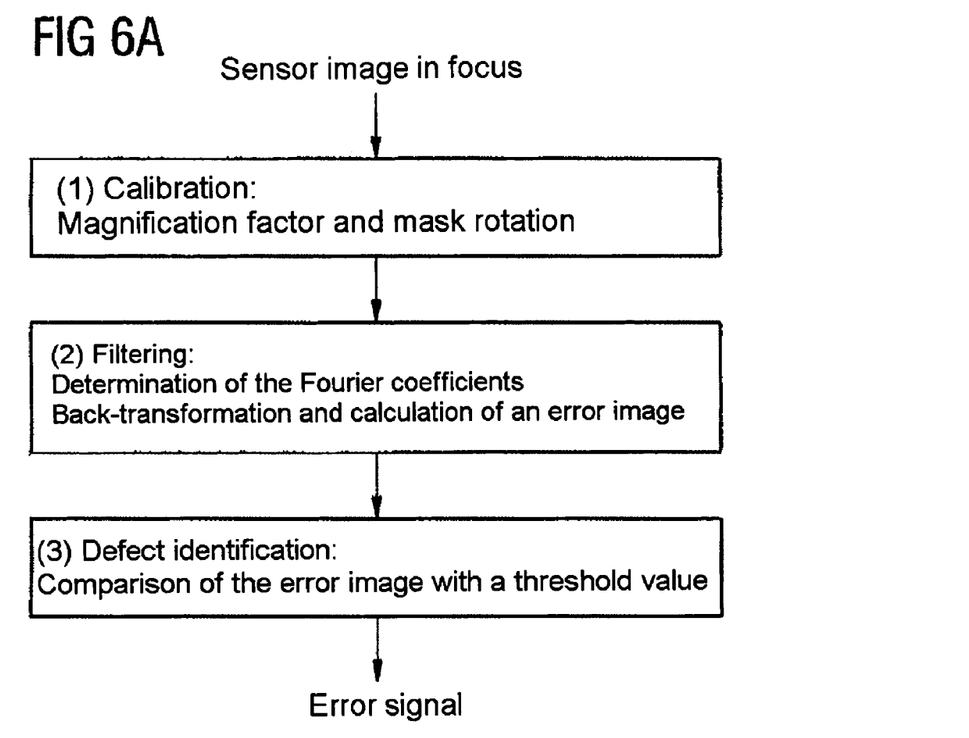
FIG. 6A shows an algorithm for finding defects in a periodic input image.
Figure 6B:
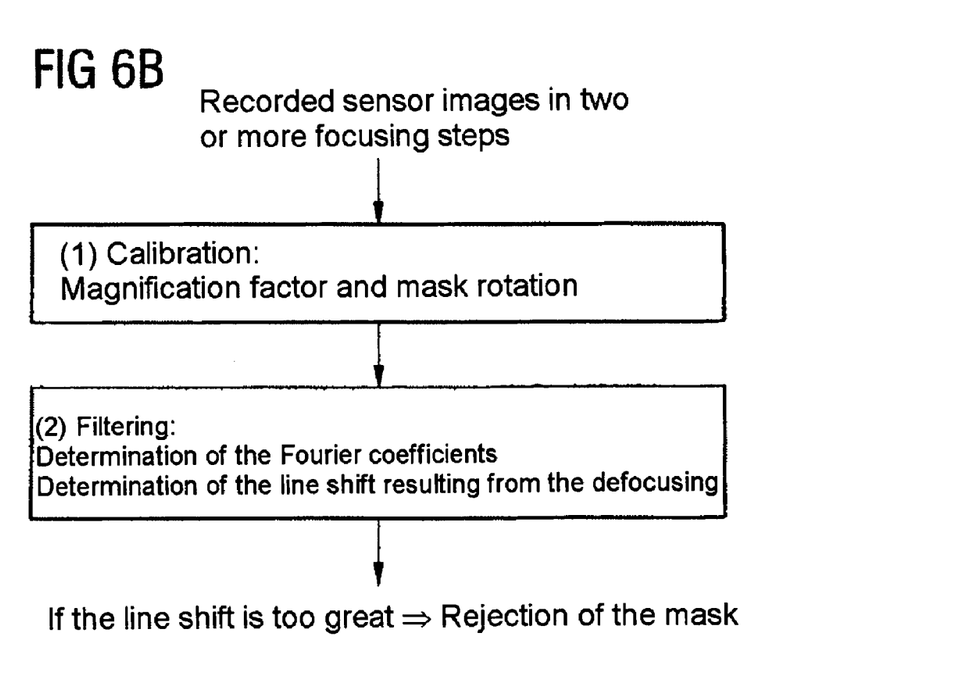
FIG. 6B shows an algorithm for qualification of alternating phase masks.

It should be noted here that the defect was not caused by the mask. This imaging disturbance was caused by a small grain of dust on the lens of the CCD camera. The associated algorithm is summarized in FIG. 6A.

Figure 4A:
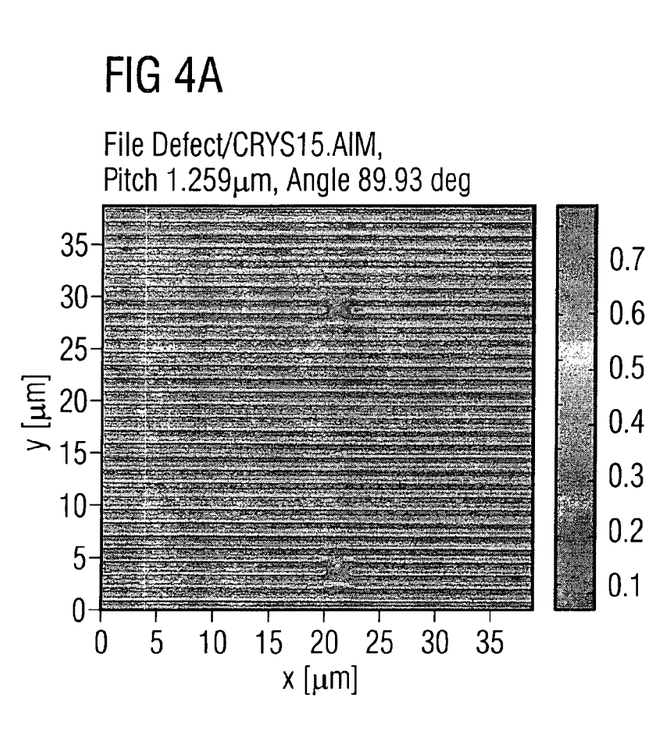
FIG. 4A shows an original image of a defective mask.
Figure 4B:
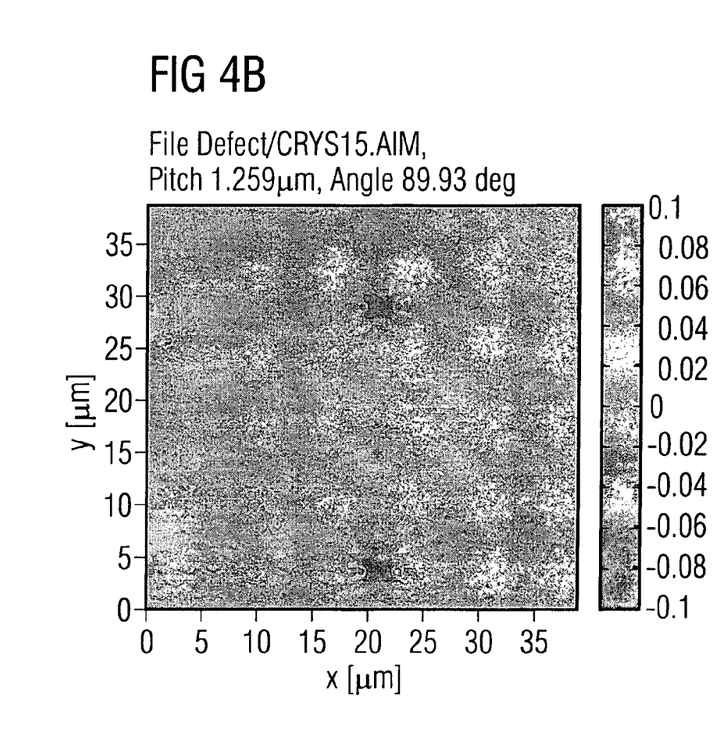
FIG. 4B shows the residual error image of the mask after image processing.

In the second example illustrated in FIGS. 4A and 4B, the Fourier filtering technology was applied to an image of a tested defective mask. As can be seen from FIG. 4A, at the side, the defects in the residual image are clearly visible and can be identified by means of a threshold value switch.

Figure 5A:
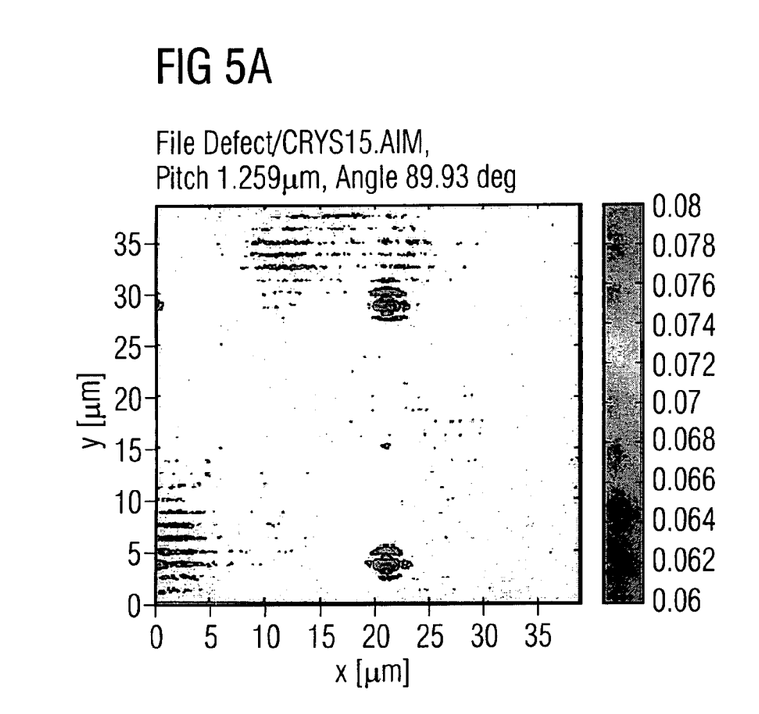
FIG. 5A shows a reproduction of the defect signals for the defective mask without filtering and with a threshold value of 6%.
Figure 5B:
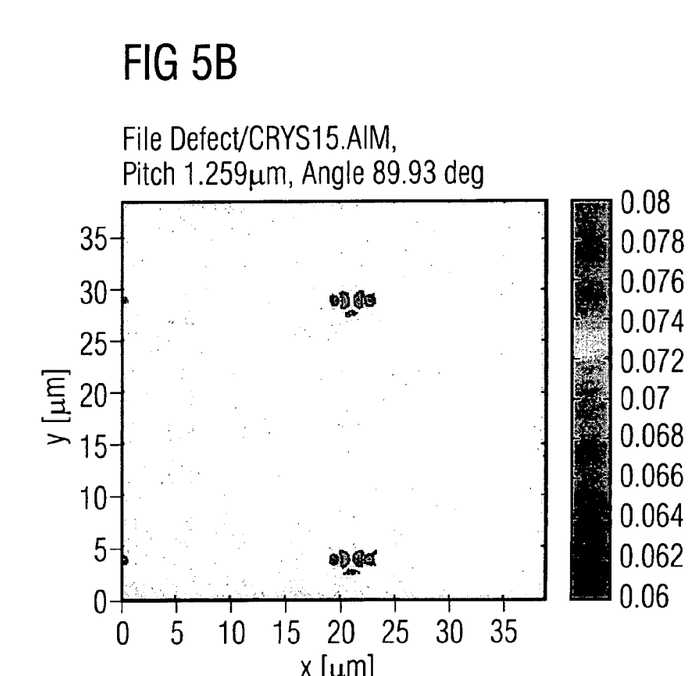
FIG. 5B shows the defect signal after filtering of the residual image, using a threshold value of 6%.

FIG. 5A shows a reproduction of the defect signals for the defective mask without filtering and using a threshold value of 6%, and FIG. 5B shows the defect signal after filtering of the residual image using a threshold value of 6%.

The examples which have been described have used only one line grating for the Fourier processing. This simplification does not restrict the method just to line gratings. It is possible to apply the method to two-dimensional gratings, such as contact holes or trench arrays. The associated algorithm is summarized in FIG. 6A.

A mask that is generated and tested according to the teachings herein can be used to manufacture a semiconductor device. For example, after the lithography mask is manufactured, it will be inspected as taught herein. To manufacture a semiconductor device, a resist material, e.g., photoresist, is formed over a semiconductor substrate. In this context, a semiconductor substrate is any semiconductor wafer with or without subsequent layers formed thereon. The resist is patterned using the lithography mask after which the semiconductor substrate is effected based on the patterning. For example, the resist could pattern an implantation mask, an etch mask, or the like. As noted above, the mask could be particularly useful in the formation of devices with repeating structures such as memory arrays.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method for inspection of periodic structures on a lithography mask using a microscope with adjustable illumination and an operating element used for movement of a mechanical stage wherein the lithography mask is attached to the mechanical stage in order to record images of the lithography mask at a computer-controlled location on the lithography mask, wherein a position, a size and a pitch specification of the mask are stored, the method comprising:
   calibrating a first image of each array structure for selected locations on the lithography mask;
   calculating Fourier coefficients at a reference point of an array/diffraction grating;
   calculating a residual image from a difference between an original image of the array structure and a Fourier expansion;
   forming a threshold value for the calculation of an image indicating an error; and
   repairing the lithography mask when an error exceeds the threshold value.

2. The method of claim 1, wherein the calibrating is carried out by determining a mask rotation and determining a magnification.

3. The method of claim 2, wherein the determining the mask rotation and the magnification are carried out by numerical optimization wherein a rotation angle and a magnification factor are chosen such that a magnitude of the associated Fourier coefficient is a maximum.

4. The method of claim 1, wherein a frequency filter is used to reduce curling in the residual image.

5. The method of claim 1, wherein the Fourier coefficients are determined and calculated in accordance with an error determination algoritlun, the method comprising:
   measuring the Fourier coefficients of a main position at a large number of points on the mask;
   converting the Fourier coefficients to a line width value by means of back-transformation and a predetermined intensity threshold value;
   determining a mean value of an error in a line width by forming an average value over all the measurement points; and
   rejecting the lithography mask if the error in the line width is greater than the predetermined threshold value.

6. The method of claim 5, wherein the determining a mean value of an error comprises:
   recording each mask position using different focal lengths;
   measuring the width of the image lines and the image lines' separations by use of Fourier analysis; and
   determining the error from the defocusing and from the difference between the adjacent intermediate spaces when the error exceeds the predetermined threshold value.

7. A method for producing a lithograpby mask, wherein the method comprises
   coating the lithography mask;
   developing the lithography mask;
   etching the lithography mask;
   inspecting the lithography mask, wherein the inspecting comprises calibrating a first image of each array structure for selected locations on the lithography mask, calculating Fourier coefficients at a reference point of an array/diffraction grating, calculating a residual image from a difference between an original image of the array structure and a Fourier expansion, and forming a threshold value for the calculation of an image indicating an error; and
   repairing the lithography mask based upon results of the inspecting.

8. The method of claim 7, wherein the lithography mask comprises a chromium mask.

9. The method of claim 7, wherein the lithography mask comprises a half-tone mask.

10. The method of claim 7, wherein the lithography mask comprises an interference mask.

11. The method of claim 7, wherein the repairing is carried out by means of ion etching.

12. The method of claim 7, wherein the repairing is cried out by use of an atom microscope for microprocessing of the lithography mask.

13. A method of manufacturing a semiconductor device, the method comprising:
   manufacturing a lithography mask;
   inspecting the lithography mask, wherein the inspecting comprises calibrating a first image of each array structure for selected locations on the lithography mask, calculating Fourier coefficients at a reference paint of an array/diffraction grating, calculating a residual image from a difference between an original image of the array structure and a Fourier expansion, and forming a threshold value for the calculation of an image indicating an error;
   forming a resist material over a semiconductor substrate;
   patterning the resist material using the lithography mask; and
   affecting the semiconductor substrate based on the patterning.

14. The method of claim 13 and further comprising repairing the lithography mask based upon results of the inspecting.

15. The method of claim 14, wherein the repairing is carried out by means of ion etching.

16. The method of claim 14, wherein the repairing is carried out by use of an atom microscope for microprocessing of the lithography mask.

17. The method of claim 13, wherein effecting the semiconductor substrate comprises forming a portion of an array of memory cells.

18. The method of claim 13, wherein the calibrating is varied out by determining a mask rotation and determining a magnification.

19. The method of claim 18, wherein the determining the mask rotation and the magnification are carried out by numerical optimization wherein a rotation angle and a magnification factor are chosen such that a magnitude of the associated Fourier coefficient is a maximum.

20. The method of claim 13, wherein the Fourier coefficients are determined and calculated in accordance with an error determination algorithm, the method comprising:
   measuring the Fourier coefficients of a main position at a large number of points on the mask;
   converting the Fourier coefficients to a line width value by means of back-transformation and a predetermined intensity threshold value;
   determining a mean value of an error in a line width by Conning an average value over all the measurement points; and
   rejecting the lithography mask if the error in the line width is greater than a predetermined threshold value.

21. The method of claim 13, wherein the determining a mean value of an error comprises:

recording each mask position using different focal lengths;

measuring the width of the image lines and the image lines' separations by use of Fourier analysis; and determining the error from the defocusing and from the difference between the adjacent intermediate spaces when the error exceeds the predetermined threshold value.

* * * * *

UNITED STATES PATENT AND TRADEMARK OFFICE
CERTIFICATE OF CORRECTION

PATENT NO. : 7,262,850 B2
APPLICATION NO. : 10/735414
DATED : August 28, 2007
INVENTOR(S) : Dettmann et al.

It is certified that error appears in the above-identified patent and that said Letters Patent is hereby corrected as shown below:

In Col. 3, line 25, delete "fat" and insert --at--.
In Col. 5, line 29, delete "maks," and insert --mask,--.
In Col. 7, line 35, delete "algoritlun," and insert --algorithm,--.
In Col. 8, line 14, delete "cried" and insert --carried--.
In Col. 8, line 23, delete "paint" and insert --point--.
In Col. 8, line 46, delete "varied" and insert--carried--.
In Col. 8, line 62, delete "Conning" and insert --forming--.

Signed and Sealed this

Thirteenth Day of November, 2007

JON W. DUDAS
*Director of the United States Patent and Trademark Office*